United States Patent
Takada et al.

(10) Patent No.: US 10,024,848 B2
(45) Date of Patent: Jul. 17, 2018

(54) FLOW CHANNEL DEVICE AND DETECTION METHOD USING SAME

(71) Applicant: Panasonic Intellectual Property Management Co., Ltd., Osaka (JP)

(72) Inventors: Akihiko Takada, Hyogo (JP); Kiyoshi Hashimotodani, Kyoto (JP); Yusuke Kitagawa, Kyoto (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 237 days.

(21) Appl. No.: 14/785,572

(22) PCT Filed: Apr. 16, 2014

(86) PCT No.: PCT/JP2014/002161
§ 371 (c)(1),
(2) Date: Oct. 19, 2015

(87) PCT Pub. No.: WO2014/174807
PCT Pub. Date: Oct. 30, 2014

(65) Prior Publication Data
US 2016/0069873 A1    Mar. 10, 2016

(30) Foreign Application Priority Data

Apr. 25, 2013   (JP) .................................. 2013-092357

(51) Int. Cl.
*G01N 33/543*    (2006.01)
*B01L 3/00*    (2006.01)
*B01J 19/00*    (2006.01)

(52) U.S. Cl.
CPC ........ *G01N 33/54366* (2013.01); *B01J 19/00* (2013.01); *B01L 3/502715* (2013.01);
(Continued)

(58) Field of Classification Search
CPC ............... B01J 19/00; B01L 2200/027; B01L 2300/0627; B01L 2300/0825;
(Continued)

(56) References Cited

U.S. PATENT DOCUMENTS

| | | |
|---|---|---|
| 2004/0166551 A1 | 8/2004 | Moulds et al. |
| 2005/0019231 A1 | 1/2005 | Kahl |
| 2008/0023324 A1 | 1/2008 | Ban et al. |
| 2011/0038758 A1 | 2/2011 | Akaba et al. |
| 2012/0028247 A1 | 2/2012 | Tamura et al. |

(Continued)

FOREIGN PATENT DOCUMENTS

| | | |
|---|---|---|
| JP | 2004-317489 | 11/2004 |
| JP | 2005-504317 | 2/2005 |

(Continued)

OTHER PUBLICATIONS

International Search Report of PCT application No. PCT/JP2014/002161 dated Jul. 22, 2014.

*Primary Examiner* — Maureen Wallenhorst
(74) *Attorney, Agent, or Firm* — McDermott Will & Emery LLP

(57) ABSTRACT

A flow channel device includes a flow channel section and an introduction channel section. The flow channel section includes a flow channel in which a detection object flows and a wall surface surrounding the flow channel. The introduction channel section includes an introduction channel having a first end connected to the flow channel and a second end connected to an introduction port, and a wall surface surrounding the introduction channel. At least a part of the wall surface surrounding the introduction channel is a curved surface protruding toward the introduction channel.

3 Claims, 9 Drawing Sheets

(52) U.S. Cl.
CPC ... *B01L 3/502761* (2013.01); *B01L 2200/027* (2013.01); *B01L 2300/0627* (2013.01); *B01L 2300/0825* (2013.01); *B01L 2300/0858* (2013.01); *B01L 2300/0861* (2013.01); *B01L 2400/0406* (2013.01); *Y10T 436/2575* (2015.01)

(58) Field of Classification Search
CPC ..... B01L 2300/0858; B01L 2300/0861; B01L 2400/0406; B01L 3/502715; B01L 3/502761; G01N 33/545; G01N 33/54366; G01N 35/08; Y10T 436/2575
USPC .............. 436/501, 518, 164, 165, 174, 180; 422/502, 503, 507; 435/5, 7.1, 287.2, 435/287.3
See application file for complete search history.

(56) References Cited

U.S. PATENT DOCUMENTS

| | | |
|---|---|---|
| 2012/0201724 A1 | 8/2012 | Miyata et al. |
| 2013/0319534 A1 | 12/2013 | Ogura |
| 2015/0343437 A1* | 12/2015 | Kitagawa .......... B01L 3/502753 435/309.1 |

FOREIGN PATENT DOCUMENTS

| | | |
|---|---|---|
| JP | 2007-248159 | 9/2007 |
| JP | 2008-051803 | 3/2008 |
| JP | 2009-150810 | 7/2009 |
| JP | 4850072 B | 1/2012 |
| JP | 2012-168115 | 9/2012 |
| WO | 2010/122776 | 10/2010 |
| WO | 2012/081072 | 6/2012 |

\* cited by examiner

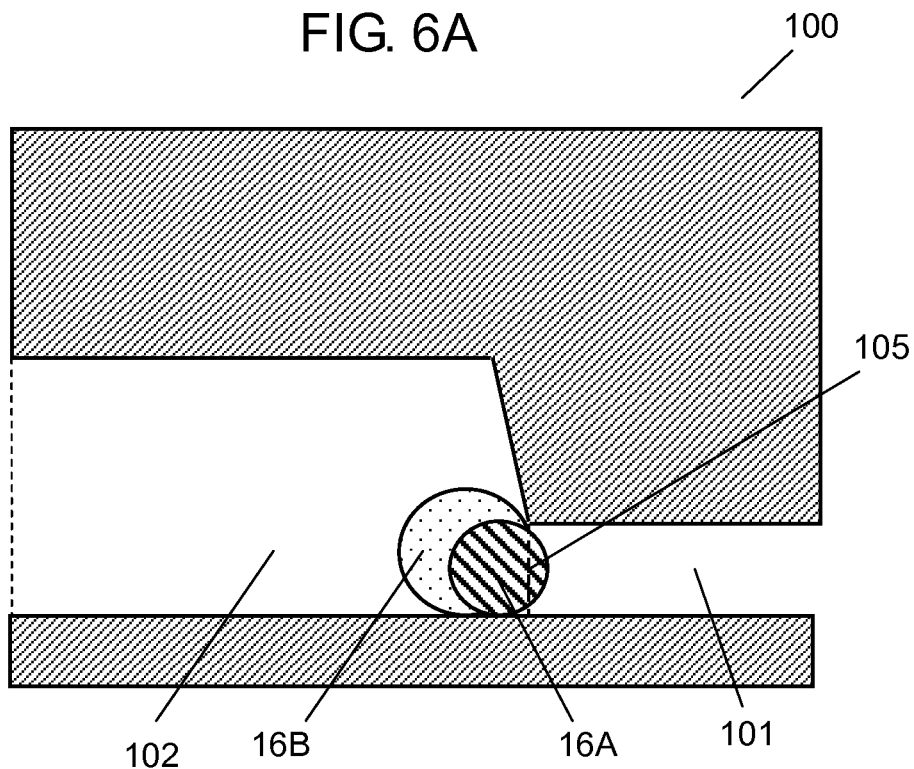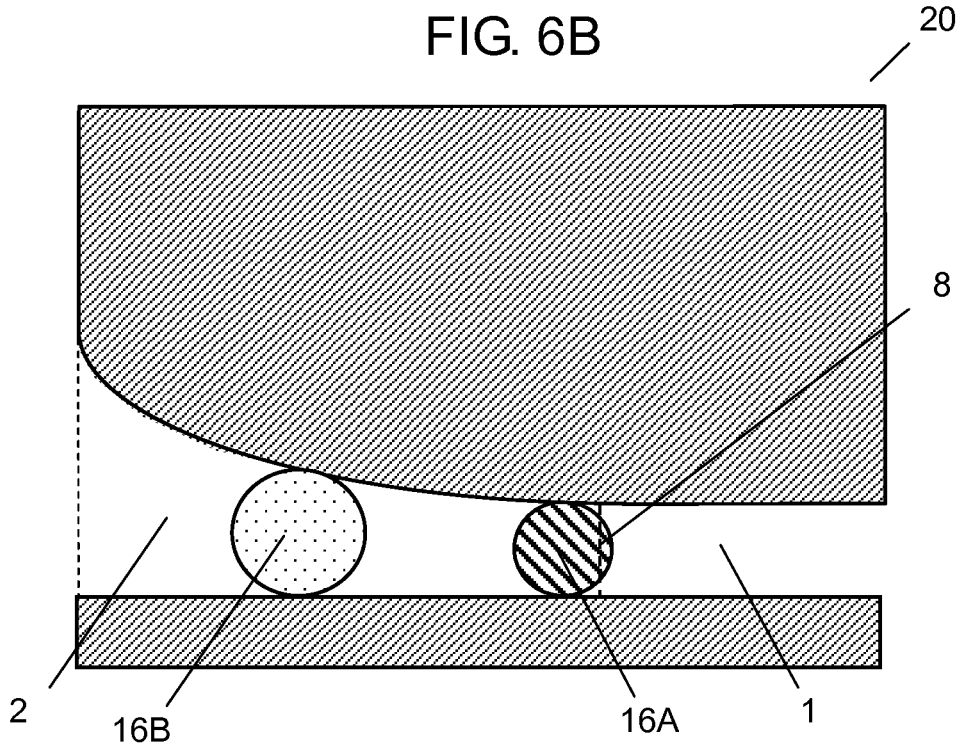

FLOW CHANNEL DEVICE AND DETECTION METHOD USING SAME

This application is a U.S. national stage application of the PCT international application No. PCT/JP2014/002161

TECHNICAL FIELD

The present technical field relates to a flow channel device that can be used for detecting a detection object (an object to be detected), such as a virus, and a detection method using the flow channel device.

BACKGROUND ART

FIG. 11 is a schematic sectional view of a conventional flow channel device 100. Flow channel device 100 includes flow channel section 111 and introduction channel section 112. Flow channel section 111 includes flow channel 101. Flow channel 101 is surrounded by a wall surface. Introduction channel section 112 includes introduction channel 102. Introduction channel 102 is surrounded by a wall surface. Introduction channel 102 has one end connected to flow channel 101, and the other end connected to introduction port 103. Introduction channel 102 is formed such that flow-channel height H10 is linearly increased from boundary surface 105 (an inlet port of flow channel 101) toward introduction port 103.

Sample 160 introduced from infusion-and-discharge port 104 is carried from introduction port 103 to flow channel 101 through introduction channel 102.

Prior art documents regarding this application include, for example, PTL 1.

CITATION LIST

Patent Literature

PLT1: International Publication WO2012/081072

SUMMARY OF THE INVENTION

A flow channel device includes a flow channel section and an introduction channel section. The flow channel section includes a flow channel in which a detection object (an object to be detected) flows, and a wall surface surrounding the flow channel. The introduction channel section includes an introduction channel having a first end connected to the flow channel and a second end connected to an introduction port, and a wall surface surrounding the introduction channel.

In the shortest direction among directions perpendicular to a direction in which the detection object flows in the flow channel, wall surfaces facing each other with the flow channel sandwiched therebetween, of the wall surface surrounding the flow channel, are defined as a first wall surface and a second wall surface. Furthermore, a wall surface adjacent to the first wall surface and a wall surface adjacent to the second wall surface, of the wall surface surrounding the introduction channel, are defined as a third wall surface and a fourth wall surface.

At least a part of the third wall surface is a curved surface protruding toward the introduction channel. A distance between the third wall surface and the fourth wall surface is larger at the second end of the introduction channel than at the first end of the introduction channel.

Furthermore, a detection method using a flow channel device includes the steps of: introducing a detection object into an introduction port; allowing the detection object to flow into an introduction channel inside the flow channel device; and then, allowing the detection object to flow into a flow channel inside the flow channel device.

BRIEF DESCRIPTION OF THE DRAWINGS

FIG. 6A is a schematic sectional view showing a boundary surface between a flow channel and an introduction channel of a conventional flow channel device.

FIG. 6B is a schematic sectional view showing the boundary surface between the flow channel and the introduction channel of the flow channel device in accordance with the exemplary embodiment.

DESCRIPTION OF EMBODIMENTS

Figure 1A:
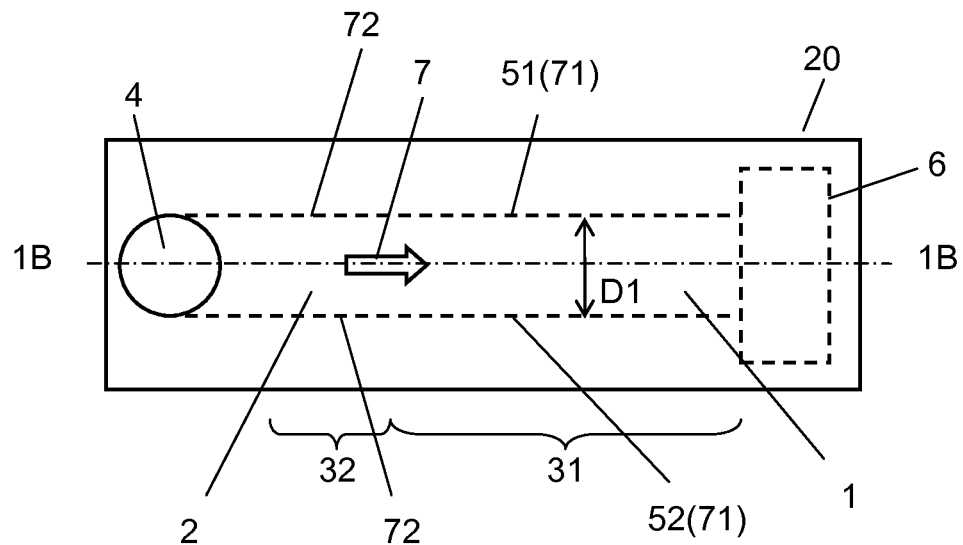
FIG. 1A is a schematic top view of a flow channel device in accordance with a first exemplary embodiment.

Before describing the exemplary embodiment, a conventional problem is described. Flow channel 101 of flow channel device 100 has a height of, for example, several tens μm or more and 1 mm or less. However, when a small amount of samples is handled, flow channel 101 is desired to have a height of several μm or less. When sample 160 including a detection object (an object to be detected) such as beads is introduced into flow channel device 100 having such a fine flow channel 101, the detection object is in close contact with a wall surface of introduction channel 102 and a wall surface of flow channel 101. When a distance between the detection object and the wall surface is short, the detection object is more influenced from the wall surface. Furthermore, a possibility that the detection object is brought into contact with the wall surface is increased. Accordingly, the detection object is easily attached to the wall surface, in particular, the wall surface in the vicinity of boundary surface 105 having a smaller height.

A flow rate of sample 160 in the vicinity of the wall surface of flow channel 101 is extremely low. Furthermore, a detection object to be introduced into flow channel device 100 is very small. Consequently, the detection object attached to the wall surface is not easily detached from the wall surface of flow channel 101. As a result, subsequently flowing detection objects are stopped by the detection object attached to the wall surface, and flow channel 101 is clogged. Thus, sample 160 including the detection object is not easily introduced into flow channel 101 and a flow of sample 160 may stagnate.

Hereinafter, exemplary embodiments for dissolving the above-described conventional problem are described with reference to drawings. Note here that the present invention is not necessarily limited to the below-mentioned contents as long as it is based on basic characteristics described in this specification.

(First Exemplary Embodiment)

Figure 1B:
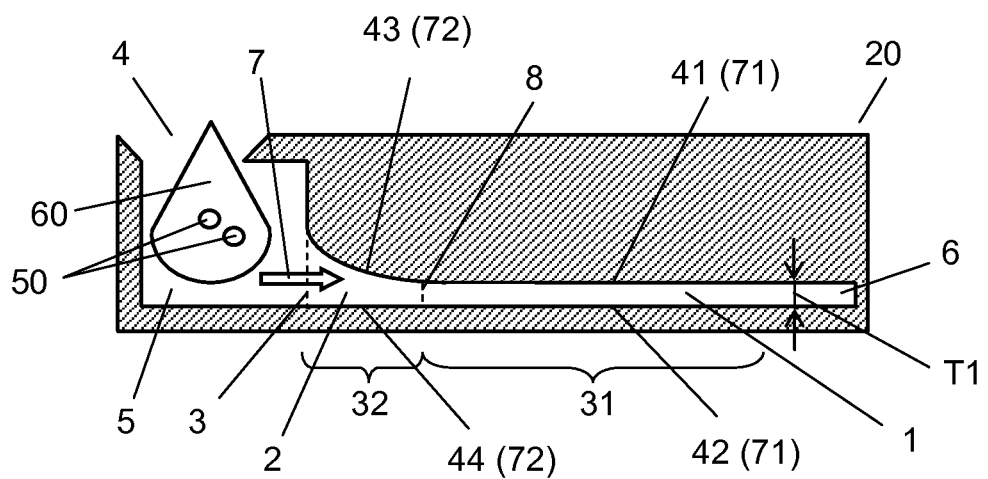
FIG. 1B is a schematic sectional view of the flow channel device in accordance with the first exemplary embodiment.

FIG. 1A is a schematic top view of flow channel device 20 in accordance with a first exemplary embodiment. FIG. 1B is a schematic sectional view of flow channel device 20 in accordance with the first exemplary embodiment. FIG. 1B schematically shows a cross-section taken on line 1B-1B of FIG. 1A.

Flow channel device 20 includes flow channel section 31 and introduction channel section 32. Flow channel section 31 includes flow channel 1 in which detection object 50 (object 50 to be detected) flows, and wall surface 71 surrounding flow channel 1. Introduction channel section 32 includes introduction channel 2 having a first end connected to flow channel 1 at boundary surface 8 and a second end connected to introduction port 3, and wall surface 72 surrounding introduction channel 2.

In the shortest direction among directions perpendicular to a direction in which detection object 50 flows (shown by arrow 7) in flow channel 1, wall surfaces facing each other with flow channel 1 sandwiched therebetween of wall surface 71 surrounding flow channel 1 are defined as first wall surface 41 and second wall surface 42. Furthermore, a wall surface adjacent to first wall surface 41 is defined as third wall surface 43, and a wall surface adjacent to second wall surface 42 is defined as fourth wall surface 44, in wall surface 72 surrounding introduction channel 2.

At least a part of third wall surface 43 is a curved surface protruding toward introduction channel 2. A distance between third wall surface 43 and fourth wall surface 44 is larger at the second end (introduction port 3) than at the first end (boundary surface 8) of introduction channel 2.

Furthermore, flow channel device 20 may include input port 4 and reservoir 5 of sample 60 at the upstream side of introduction port 3. Flow channel device 20 may include discharging region 6 at the downstream side of flow channel 1.

Sample 60 including detection object 50 is introduced into input port 4. Sample 60 introduced into input port 4 is temporarily stored in reservoir 5. The stored sample 60 flows, as shown by arrow 7, from introduction port 3 to flow channel 1 through introduction channel 2, and reaches discharging region 6. Detection object 50 is detected in flow channel 1 or discharging region 6.

Figure 2:
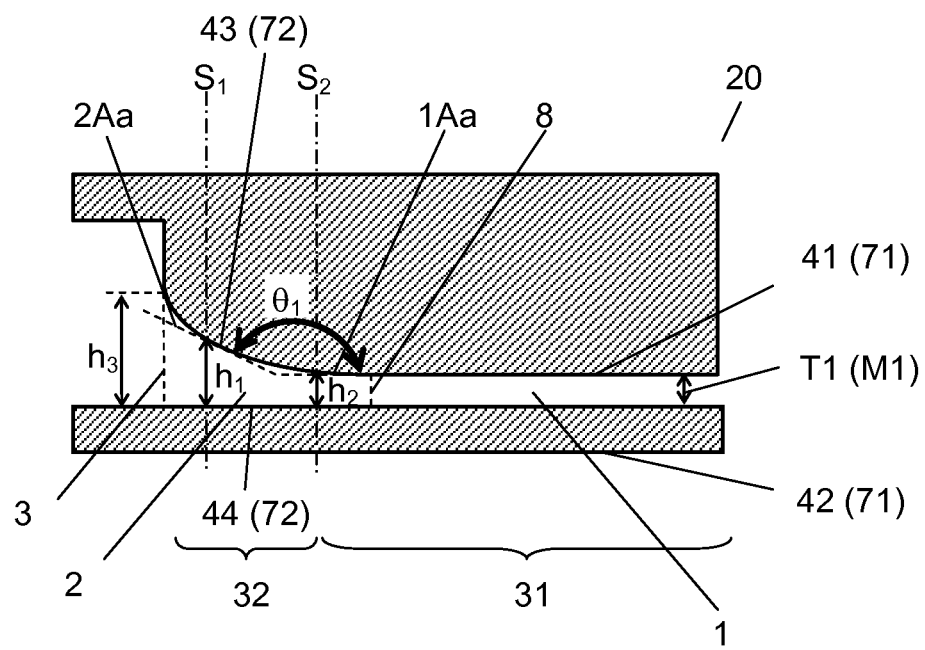
FIG. 2 is a view for illustrating a main part of the flow channel device in accordance with the first exemplary embodiment.

Hereinafter, flow channel device 20 in accordance with the first exemplary embodiment is described in detail. FIG. 2 is a view for illustrating a main part of flow channel device 20 in accordance with the first exemplary embodiment. FIG. 2 shows enlarged flow channel section 31 and introduction channel section 32 of FIG. 1B.

Herein, third wall surface 43 has a curved surface protruding toward introduction channel 2. Note here that a shape of the curved surface is preferably smooth. When the shape of the curved surface is made smooth, resistance between sample 60 and third wall surface 43 can be reduced. Furthermore, in introduction channel 2, the distance between third wall surface 43 and fourth wall surface 44 surrounding introduction channel 2 in the shortest direction among the directions perpendicular to the direction in which detection object 50 flows is increased from boundary surface 8 (the inlet port of flow channel 1) toward introduction port 3. Herein, the shortest direction among the directions perpendicular to the direction in which detection object 50 flows is a direction in which a distance between confronting wall surfaces 71 of flow channel 1 is minimum.

From the above-mentioned configuration, a distance between detection object 50 and wall surface 72 can be made larger than a distance between detection object 50 and wall surface 71. Accordingly, detection object 50 is less influenced by the wall surface at introduction port 3, and the possibility that detection object 50 and the wall surface are brought into contact with each other is also reduced. As a result, detection object 50 is not easily attached to the wall surface.

Furthermore, when a part of third wall surface 43 of introduction channel section 32 is made to be a curved surface protruding toward introduction channel 2, resistance between sample 60 and the wall surface is reduced as compared with a case where the wall surface of introduction channel 2 is flat. Therefore, a flow of sample 60 from introduction channel 2 to flow channel 1 is promoted. When the flow of sample 60 in introduction channel 2 is promoted, the flow rate at boundary surface 8 between flow channel 1 and introduction channel 2 is increased. As a result, clogging with detection object 50 is suppressed. Consequently, sample 60 including detection object 50 is introduced into flow channel 1 efficiently.

Flow channel 1 includes first wall surface 41 (the upper wall surface), second wall surface 42 (the lower wall surface), and lateral wall surfaces 51 and 52 (see FIG. 1A). Flow channel width D1 of flow channel 1 is a distance between confronting lateral wall surfaces 51 and 52. Furthermore, flow channel height T1 is a distance between confronting first wall surface 41 and second wall surface 42 in flow channel 1. When flow channel width D1 is larger than flow channel height T1, the shortest direction among the directions perpendicular to the direction in which detection object 50 flows is the height direction of flow channel device 20. In the description below, the shortest direction among the directions perpendicular to the direction in which detection object 50 flows is the height direction of flow channel 1. Note here that when flow channel width D1 is larger than flow channel height T1, even if introduction channel 2 becomes larger from boundary surface 8 to introduction port 3 only in the width direction in the top view, the effect of the present invention cannot be sufficiently achieved. This is because a factor of causing clogging of flow channel 1 with detection object 50 is determined by a relative relation of minimum distance M1 between confronting wall surfaces 71 in flow channel 1 and a dimension of detection object 50. Therefore, when flow channel width D1 is larger than flow channel height T1, in introduction channel 2, at least the height direction of flow channel device 20, that is, the shortest direction among the directions perpendicular to the direction in which detection object 50 flows needs to be larger.

In this exemplary embodiment, as mentioned above, a case where flow channel width D1 is larger than flow channel height T1 is described as an example. Accordingly, the shortest direction among directions perpendicular to the direction in which detection object 50 flows is the height direction. However, the shortest direction among the directions perpendicular to the direction in which detection object 50 flows is not necessarily limited to the height direction. For example, when flow channel width D1 is smaller than flow channel height T1, the shortest direction among the directions perpendicular to the direction in which detection object 50 flows is the width direction of flow channel device 20.

Herein, it is desirable that minimum distance M1 between first wall surface 41 and second wall surface 42 which face each other with flow channel 1 sandwiched therebetween be 5 μm or less. When minimum distance M1 is 5 μm or less, the distance between detection object 50 and wall surface 71 surrounding flow channel 1 is small. Thus, the effect of this exemplary embodiment appears remarkably. At this time, the maximum dimension of detection object 50 is 5 μm or less and more preferably 2 μm or less. Furthermore, when minimum distance M1 is 1 μm or less, the effect of this exemplary embodiment becomes more remarkable. The maximum dimension of detection object 50 to be used in flow channel device 20 is smaller than minimum distance M1. Therefore, when minimum distance M1 of flow channel 1 is 1 μm or less, the maximum dimension of detection object 50 is also 1 μm or less. When detection object 50 is 1 μm or less, detection object 50 attached to wall surface 71 by physical or chemical interaction is not easily detached from wall surface 71 even with a presence of a flow in flow channel 1. When detection object 50 is attached to wall surface 71, detection object 50 forms a lump on detection object 50 as a core, thus increasing the possibility that flow channel 1 is clogged. Even in such a case, when introduction channel 2, in which a distance between third wall surface 43 and fourth wall surface 44 is increased from boundary surface 8 to introduction port 3, is formed, the vicinity of introduction port 3 is not easily clogged with detection object 50. Therefore, the flow of sample 60 from introduction port 3 to flow channel 1 does not easily stagnate, and, therefore, detection object 50 is not easily attached to wall surface 71 of flow channel 1. Consequently, sample 60 can be introduced into flow channel 1 efficiently. In flow channel device 20 of this exemplary embodiment, sample 60 only needs to be introduced into flow channel 1, and the size of minimum distance M1 is not particularly limited.

Herein, flow channel 1 is formed such that the distances between the confronting wall surfaces 71 of flow channel 1 are substantially the same. The substantially the same distances include not only identical distances but also, for example, slightly narrower and wider flow channel height T1 and flow channel width D1. For example, flow channel height T1 or flow channel width D1 may be increased/decreased by about 5%. Furthermore, the shape of flow channel 1 includes a polyhedron such as a rectangular parallelepiped, a cylindrical shape, an elliptic cylindrical shape, and the like. Furthermore, flow channel section 31 is made of, for example, glass, resin, silicon, plastic, metal, or the like.

Flow channel 1 is formed so as to be coupled to introduction channel 2. Introduction port 3 is provided at an opposite side to flow channel 1 in introduction channel 2. Introduction port 3 is provided in parallel to boundary surface 8, that is, the longitudinal section of flow channel 1.

In this exemplary embodiment, third wall surface 43 of introduction channel section 32 and first wall surface 41 of flow channel section 31 are preferably connected to each other smoothly. When a connection portion between introduction channel 2 and flow channel 1 is made smooth, the vicinity of boundary surface 8 is not easily clogged with detection object 50. Accordingly, sample 60 can be introduced into flow channel 1 more efficiently.

Furthermore, in introduction channel 2, angle $\theta_1$ made by extension plane 1Aa of first wall surface 41 and at least one contact plane 2Aa of third wall surface 43 is an obtuse angle. It is more preferable that angle $\theta_1$ is 120° or more and less than 180°. Such a configuration allows sample 60 to flow more gently in introduction channel 2. As a result, sample 60 can be introduced from introduction channel 2 to flow channel 1 efficiently. In particular, when angle $\theta_1$ is 140° or more and less than 180°, resistance in introduction channel 2 is further reduced, so that the number of detection objects 50 to be introduced into flow channel 1 is increased. Furthermore, when angle $\theta_1$ is 150° or more and less than 180°, aggregated detection object 50 can be easily dispersed in introduction channel 2. Furthermore, it is still further preferable that angle $\theta_1$ is 160° or more and less than 180° because aggregation of detection objects 50 by wall surface 72 surrounding introduction channel 2 can be suppressed. Note here that angle $\theta_1$ may be defined as angle $\theta_1$ made by extension plane 1Aa of first wall surface 41 and contact plane 2Aa from boundary surface 8 to introduction port 3.

Figure 3A:
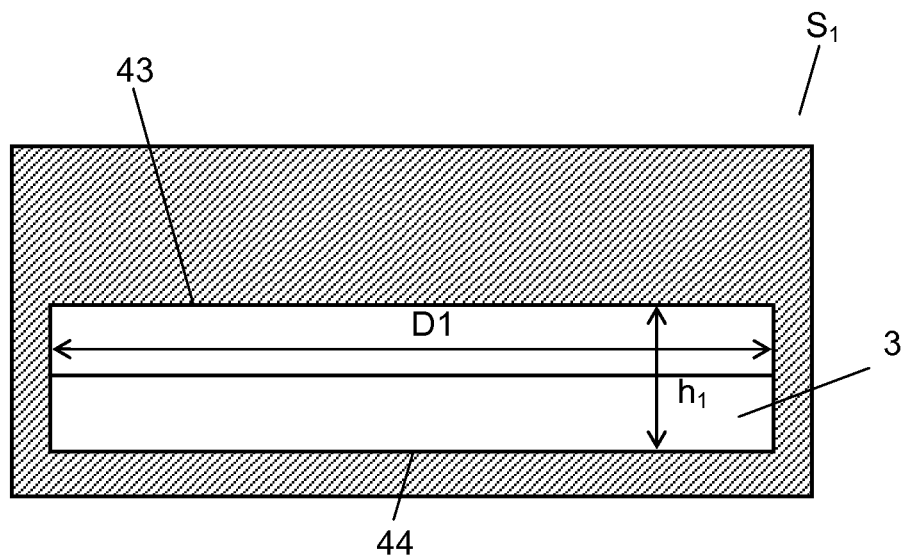
FIG. 3A is a sectional view taken on an introduction port of an introduction channel section of the flow channel device in accordance with the first exemplary embodiment.
Figure 3B:
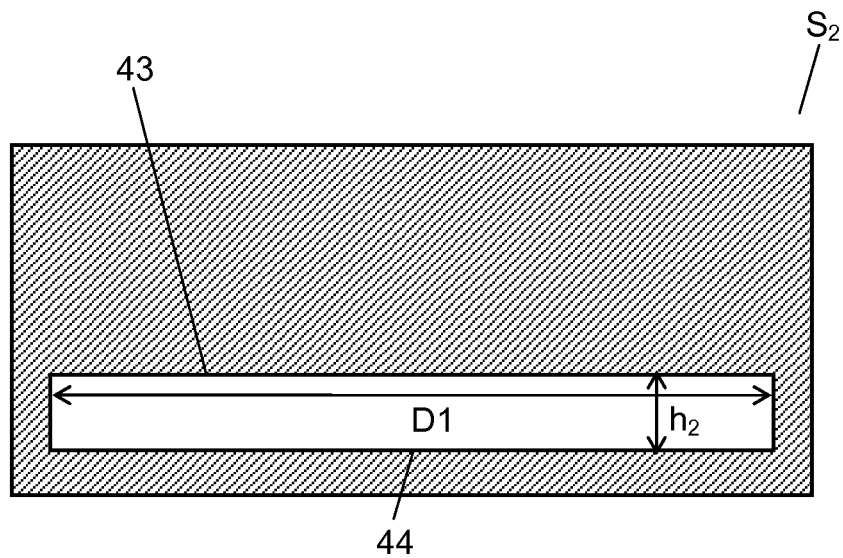
FIG. 3B is a sectional view taken on a boundary surface of the introduction channel section of the flow channel device in accordance with the first exemplary embodiment.

FIG. 3A is a view showing cross-section $S_1$ on introduction port 3 of introduction channel section 32 of flow channel device 20 in accordance with the first exemplary embodiment. FIG. 3B is a view showing cross-section $S_2$ on boundary surface 8 of introduction channel section 32 in flow channel device 20 in accordance with the first exemplary embodiment.

The minimum distance between confronting wall surfaces on cross-section $S_1$ is distance $h_1$ between third wall surface 43 and fourth wall surface 44. The minimum distance between confronting wall surfaces on cross-section $S_2$ is distance $h_2$ between third wall surface 43 and fourth wall surface 44. Distance $h_1$ between the confronting wall surfaces on cross-section $S_1$ at introduction port 3 is larger than distance $h_2$ between the confronting wall surfaces on cross-section $S_2$ of boundary surface 8.

In this way, in the shortest direction among the directions perpendicular to the direction in which detection object 50 flows, the distance between third wall surface 43 and fourth wall surface 44 in introduction channel section 32 is increased from boundary surface 8 toward introduction port 3.

This exemplary embodiment shows introduction channel section 32 having a protruding curved surface in one place. However, introduction channel section 32 may have a protruding curved surface not only in one place but also in several places. Furthermore, in addition to the case where the entire region of introduction channel section 32 has one protruding curved surface, a part of region of introduction channel section 32 may have one protruding curved surface. For example, in a flow channel device including introduction channel 2 having a total length of 2 mm or more, a protruding curved surface may be formed in a zone of 2 mm from boundary surface 8 toward introduction port 3. Furthermore, for example, in a flow channel device including introduction channel 2 having a total length of 2 mm or less, a protruding curved surface may be formed in a zone of half-length of the total length of introduction channel 2 from boundary surface 8. Furthermore, distance $h_3$ between the confronting wall surfaces in the shortest direction among the directions perpendicular to the direction in which detection object 50 flows is larger than flow channel height T1 of flow channel 1 (see FIG. 2). Herein, distance $h_3$ is a distance between an extension plane of contact plane 2Aa of third wall surface 43 and an extension plane of fourth wall surface 44 in reservoir 5.

Introduction channel section 32 is formed of, for example, glass, resin, silicon, plastic, metal, or the like. Note here that material constituting introduction channel section 32 may be different from material constituting flow channel section 31. However, it is preferable that flow channel section 31 and introduction channel section 32 are formed of the same material because flow channel section 31 and introduction channel section 32 can be formed simultaneously.

Herein, examples of detection object 50 include fine particles such as beads, latex particles, metal particles, cells such as blood cells, or the like. It is desirable that the size of detection object 50 be 10 µm or less. Furthermore, fine particles may be modified with an antibody.

Figure 4:
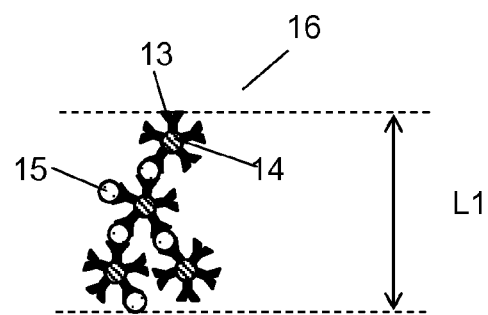
FIG. 4 is a schematic view of an aggregate in accordance with the first exemplary embodiment.

FIG. 4 is a schematic view of aggregate 16 in accordance with the first exemplary embodiment. Fine particles 14 having a surface modified with antibody 13 bind to antigen 15 contained in sample 60 through an antigen-antibody reaction so as to form aggregate 16. Herein, fine particles 14 or aggregate 16 correspond to detection object 50.

When antigen 15 specifically binding to antibody 13 is contained in sample 60, fine particles 14 modified with antibody 13 form aggregate 16 through an antigen-antibody reaction. Note here that fine particles 14 modified with antibody 13 may be mixed with sample 60. Furthermore, a predetermined number of fine particles 14 modified with antibody 13 may be previously fixed to reservoir 5, introduction channel 2, flow channel 1, or the like.

Figure 5:
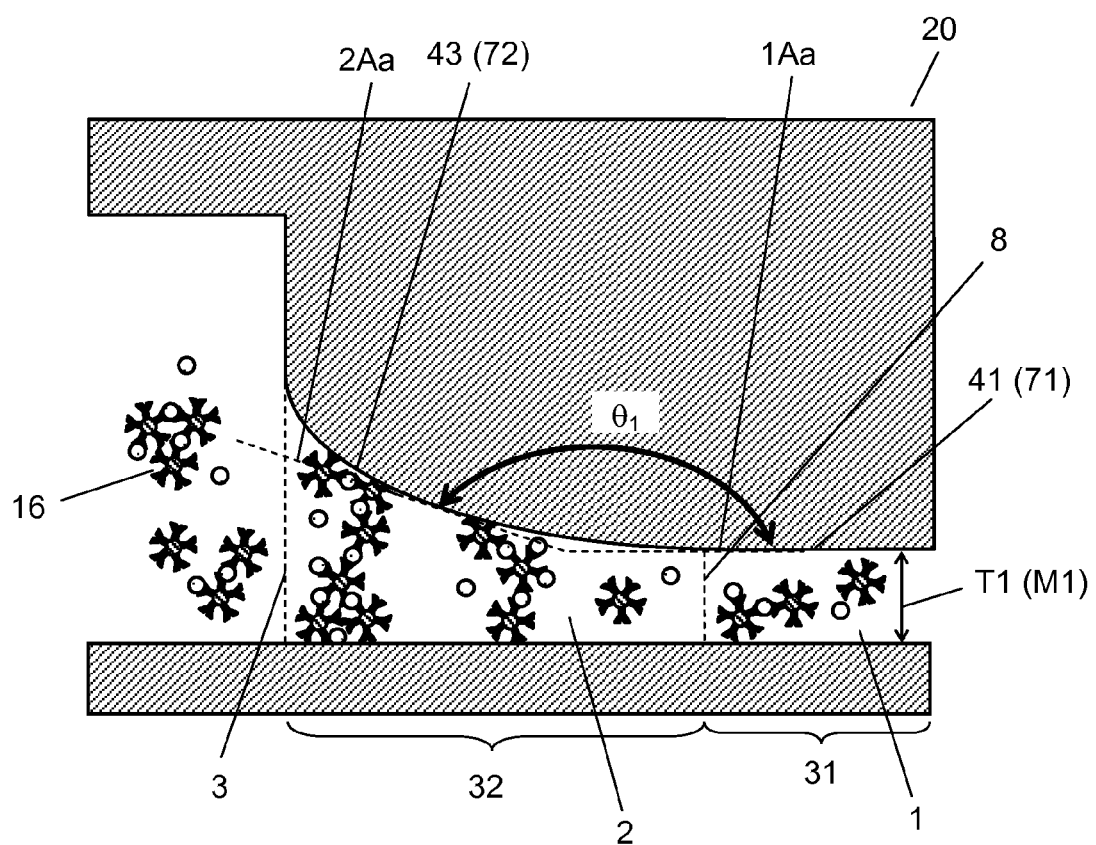
FIG. 5 is a schematic view showing movement of the aggregate introduced into the flow channel device in accordance with the first exemplary embodiment.

FIG. 5 is a schematic view showing movement of aggregates 16 introduced into flow channel device 20 in accordance with the first exemplary embodiment. FIG. 5 schematically shows a state in which sample 60 containing aggregates 16 is introduced into flow channel 1. Sample 60 is omitted in FIG. 5.

In flow channel device 20, as described in FIG. 2, angle $\theta_1$ made by extension plane 1Aa of first wall surface 41 of flow channel section 31 and at least one contact plane 2Aa of third wall surface 43 is an obtuse angle. Furthermore, in introduction channel 2, the height of introduction channel 2 is increased from boundary surface 8 toward introduction port 3. That is to say, the minimum distance between third wall surface 43 and fourth wall surface 44 is larger at introduction port 3 than at boundary surface 8.

When fine particles 14 modified with antibody 13 form aggregate 16 through an antigen-antibody reaction, the size of aggregate 16 varies depending on the degree of proceeding of the reaction. In order to introduce aggregate 16 into flow channel 1, maximum dimension L1 of aggregate 16 is required to be smaller than minimum distance M1 between confronting wall surfaces 71 of flow channel 1. However, aggregate 16 having maximum dimension L1 larger than minimum distance M1 may be formed depending on the degree of proceeding of the reaction. Aggregate 16 having maximum dimension L1 larger than minimum distance M1 may cause clogging at boundary surface 8, thus causing stagnation of the flow of sample 60.

However, flow channel device 20 has a configuration in which a distance between the confronting wall surfaces of introduction channel 2 is increased from boundary surface 8 toward introduction port 3. Therefore, aggregate 16 having maximum dimension L1 larger than minimum distance M1 of flow channel 1 stops not only at boundary surface 8 but also in introduction channel 2. In this way, aggregates 16 are dispersed in introduction channel 2 depending upon the dimension of aggregates 16. As a result, sample 60 flows in the width direction in introduction channel 2 and flow channel 1, so that stagnation of the flow of sample 60 can be prevented. Therefore, in flow channel device 20, sample 60 containing aggregates 16 can be introduced into flow channel 1 efficiently.

The above-mentioned configuration is described with reference to schematic views.

FIG. 6A is a schematic sectional view showing boundary surface 105 between flow channel 101 and introduction channel 102 of conventional flow channel device 100. FIG. 6B is a schematic sectional view showing boundary surface 8 between flow channel 1 and introduction channel 2 of flow channel device 20 in accordance with this exemplary embodiment. In FIGS. 6A and 6B, aggregates having different sizes are referred to as aggregates 16A and 16B. For simplification, aggregates 16A and 16B are shown by a circle, respectively.

As shown in FIG. 6A, in conventional flow channel device 100, almost all of aggregates 16A and 16B having a larger dimension than flow channel 101 stop at boundary surface 105. Therefore, in boundary surface 105, aggregates 16A and 16B having different sizes are arranged in the lateral direction of flow channel device 100. As a result, flow channel 1 is blocked at boundary surface 105, and the flow of sample 60 stagnates.

On the contrary, in this exemplary embodiment, as shown in FIG. 6B, aggregates 16A and 16B having different sizes stop at different places in the sectional view of flow channel device 20. As a result, flow channel 1 is not blocked at boundary surface 8, and the flow of samples 60 does not stagnate.

Furthermore, when an antigen-antibody reaction occurs inside introduction channel 2 and fine particles 14 form aggregate 16, aggregate 16 is formed in a state in which it is surrounded by wall surfaces 72. Therefore, growth of aggregate 16 in the longitudinal direction is suppressed. Consequently, flow channel device 20 can suppress the formation of aggregate 16 having maximum dimension L1 larger than distance $h_3$.

Furthermore, when the minimum distance between confronting wall surfaces 71 of flow channel 1 is smaller than 30 times as large as the maximum dimension of detection object 50, aggregate 16 starts to stop in introduction channel section 32. Therefore, it is useful to provide introduction channel section 32. Furthermore, when the minimum distance between confronting wall surfaces 71 of flow channel 1 is smaller than ten times as large as the maximum dimension of detection object 50, flow channel 1 may be blocked when aggregate 16 is allowed to flow without introduction channel section 32. Therefore, an effect of providing introduction channel section 32 can be found remarkably. Furthermore, when the minimum distance between confronting wall surfaces 71 of flow channel 1 is smaller than five times as large as the maximum dimension of detection object 50, even when not-aggregated detection object 50 is attached to boundary surface 8, flow channel 1 may be blocked without introduction channel section 32. Therefore, the effect of providing introduction channel section 32 becomes remarkable. Furthermore, when the minimum distance between confronting wall surfaces 71 of flow channel 1 is larger to some extent as compared with the maximum dimension of detection object 50, an influence on detection object 50 from the wall surfaces and the possibility that detection object 50 and the wall surface are brought into contact with each other are reduced. Even if detection object 50 is attached to the wall surface, since the minimum distance between the confronting wall surfaces of flow channel 1 is relatively large, the possibility that flow channel 1 is clogged with detection object 50 is small. However, when the minimum distance between confronting wall surfaces 71 of flow channel 1 is smaller than 30 times as large as the maximum dimension of detection object 50, an influence on detection object 50 from the wall surfaces becomes larger. When the distance between detection object 50 and the wall surface becomes smaller, the possibility that detection object 50 is brought into contact with the wall surface is accordingly increased. Therefore, detection object 50 is easily attached to the wall surface of flow channel 1. Then, when the minimum distance between confronting wall surfaces 71 of flow channel 1 is the same level as the maximum dimension of detection object 50, flow channel 1 may be easily clogged with detection object 50 attached to the wall surface. However, when flow channel device 20 is provided with introduction channel 2 in which the minimum distance between the wall surfaces is increased from the boundary surface 8 to introduction port 3, the vicinity of introduction port 3 is not easily clogged with detection object 50. That is to say, since sample 60 flows from introduction port 3 to flow channel 1, attachment of detection object 50 to the wall surfaces of flow channel 1 can be suppressed. Therefore, sample 60 including detection object 50 can be introduced into flow channel 1 efficiently.

Figure 7:
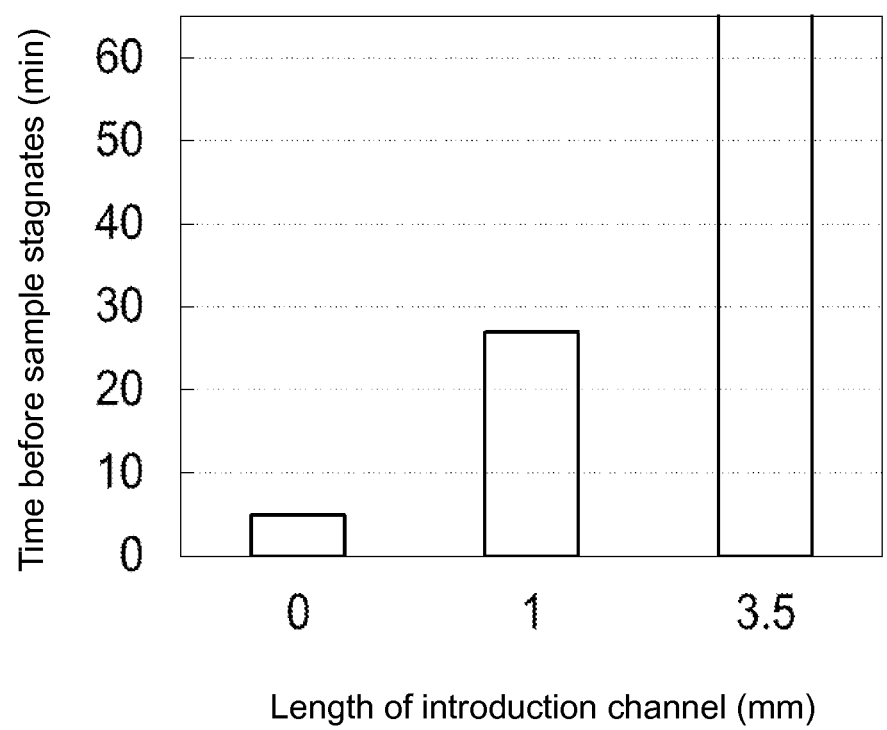
FIG. 7 is a graph showing a relation between a length of the introduction channel and time before a flow of a sample stagnates.

Herein, FIG. 7 shows a relation between a length of introduction channel 2 and time before flow channel 1 is clogged with detection object 50 and the flow of sample 60 stagnates when sample 60 is introduced into flow channel device 20. As shown in FIG. 7, when introduction channel 2 is not provided, the flow of sample 60 stagnates in five minutes. However, when introduction channel 2 having a length of 1 mm is provided, sample 60 flows for 27 minutes. If sample 60 can be allowed to flow for 25 minutes or more, sample 60 can be sufficiently introduced into flow channel 1. Therefore, the length of introduction channel 2 is desirably 1 mm or longer. Furthermore, when introduction channel 2 having a length of 3.5 mm is provided, sample 60 continues to flow for 60 minutes or more. When introduction channel 2 has a length of 3.5 mm, the flow of sample 60 can be kept high. Accordingly, time required to introduce sample 60 into flow channel 1 can be shortened. Therefore, it is desirable that introduction channel 2 be 3.5 mm or more. Thus, the longer the length of introduction channel 2 becomes, the longer the time before sample 60 stagnates becomes. Note here that when the length of introduction channel 2 becomes longer, the size of a device itself becomes larger. Therefore, it is desirable that the length of introduction channel 2 be 20 mm or less.

Figure 8:
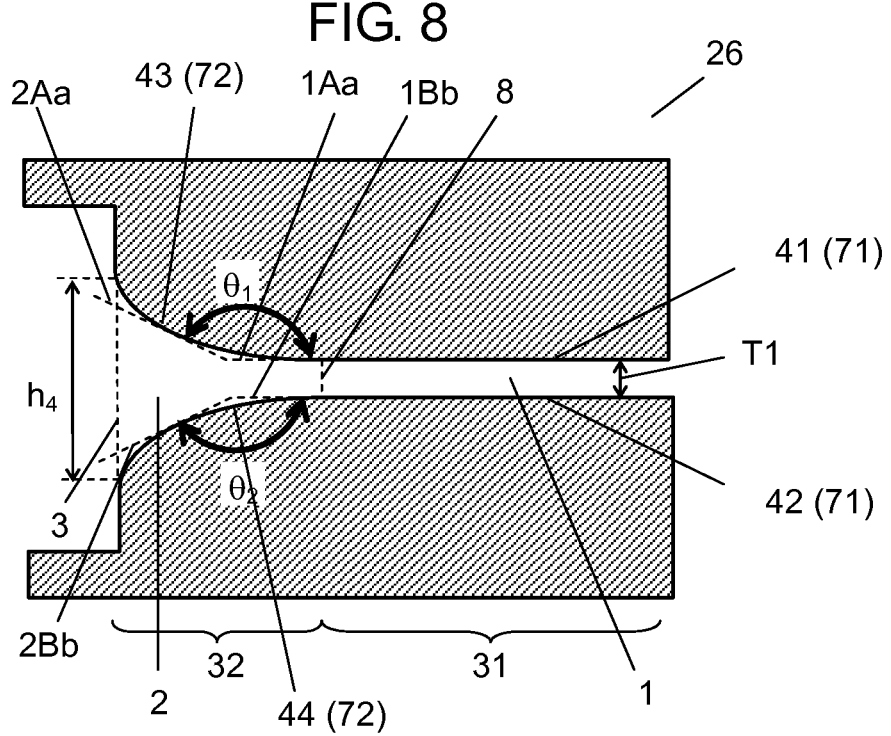
FIG. 8 is a schematic sectional view of another flow channel device in accordance with the first exemplary embodiment.

FIG. 8 is a schematic sectional view of another flow channel device 26 in accordance with the first exemplary embodiment. As shown in FIG. 8, introduction channel 2 may be formed such that it is widened toward the upper and lower sides from boundary surface 8 toward introduction port 3. Angle $\theta_2$ made by extension plane 1Bb of second wall surface 42 of flow channel section 31 and at least one contact plane 2Bb of fourth wall surface 44 of introduction channel section 32 is an obtuse angle. It is desirable that angle $\theta_2$ be 120° or more and less than 180°. Furthermore, angle $\theta_2$ may be the same as or different from angle $\theta_1$. With such a configuration, distance $h_4$ can be increased. Herein, distance $h_4$ is a distance between an extension plane of contact plane 2Aa of third wall surface 43 and contact plane 2Bb of fourth wall surface 44 in reservoir 5. As a result, the vicinity of introduction port 3 is not easily clogged with detection object 50. Therefore, the flow of sample 60 from introduction port 3 to flow channel 1 does not stagnate, and sample 60 including detection object 50 can be introduced into flow channel 1 efficiently.

Furthermore, introduction channel 2 may be formed such that the distance between confronting third wall surface 43 and fourth wall surface 44 is increased from boundary surface 8 to introduction port 3 in the direction other than the shortest direction among the directions perpendicular to the direction in which detection object 50 flows, in a cross-section parallel to boundary surface 8. This configuration can suppress clogging with detection object 50 in the vicinity of introduction port 3.

(Second Exemplary Embodiment)

Hereinafter, flow channel device 28 in accordance with a second exemplary embodiment is described with reference to drawings.

Figure 9:
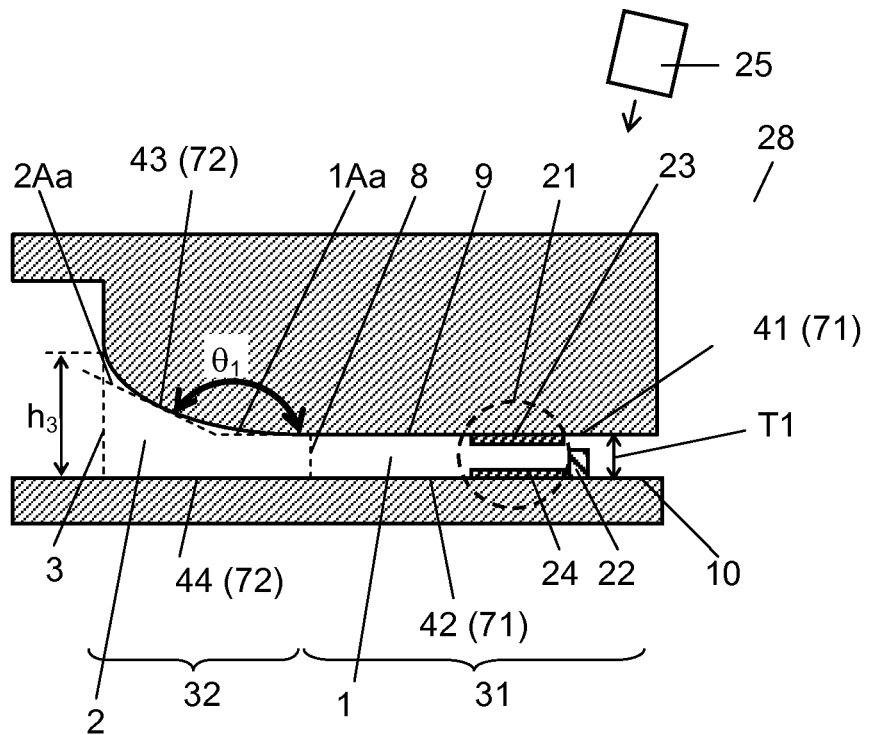
FIG. 9 is a schematic sectional view of a flow channel device in accordance with a second exemplary embodiment.

FIG. 9 is a schematic sectional view of flow channel device 28 in accordance with the second exemplary embodiment. Note here that the same reference numerals are given to the same configuration of the first exemplary embodiment, and description thereof is not repeated.

Flow channel device 28 includes detection region 21 for detecting detection object 50 in flow channel 1, and also includes barrier 22, on which detection object 50 accumulate, at a downstream side of detection region 21.

Barrier 22 is provided in flow channel 1 such that the minimum distance between confronting wall surfaces 71 of flow channel 1 is smaller than the maximum dimension of detection object 50. Therefore, detection object 50 such as a fine particle and an aggregate cannot pass through a gap between barrier 22 and wall surface 71, and detection object 50 is accumulated in detection region 21. Then, the accumulated detection object 50 is detected.

Note here that barrier 22 may be provided such that the gap between barrier 22 and wall surface 71 becomes larger than a fine particle and smaller than an aggregate. In this case, detection object 50 is an aggregate. It is possible to detect whether or not fine particles form an aggregate. In the case where fine particles are modified with an antibody, when an aggregate is formed, it is possible to detect whether or not the sample includes an antigen.

Furthermore, in detection region 21, first metal layer 23 is formed on first wall surface 41. Then, second metal layer 24 is formed on second wall surface 42 confronting first wall surface 41. That is to say, the metal layers are formed so as to sandwich flow channel 1 therebetween in at least a part of wall surfaces 71 surrounding flow channel 1. Note here that first metal layer 23 and second metal layer 24 may be formed only in detection region 21, or may be formed throughout the entire flow channel 1.

First metal layer 23 and second metal layer 24 are made of metal such as gold and silver.

Electromagnetic wave source 25 is disposed a part above first metal layer 23. Herein, the part above first metal layer 23 denotes a direction opposite to second metal layer 24 with respect to first metal layer 23. Electromagnetic wave source 25 irradiates detection region 21 with electromagnetic wave from the part above first metal layer 23. Irradiated electromagnetic waves are reflected by first metal layer 23 and second metal layer 24, respectively. A user can detect presence or absence of detection object 50 by detecting a change in interference of two reflected electromagnetic waves. Herein, it is desirable that the electromagnetic wave with which flow channel device 28 is irradiated be visible light.

A film thickness of first metal layer 23 is about 100 nm or less. When first metal layer 23 is formed of gold, it is desirable that the film thickness of first metal layer 23 be 5 nm or more and 15 nm or less.

When second metal layer 24 is formed of gold, it is desirable that the film thickness of second metal layer 24 be 100 nm or more. This is because when the film thickness of second metal layer 24 is less than 100 nm, entering electromagnetic wave (visible light) passes through second metal layer 24 and an amount of electromagnetic waves to be reflected into flow channel 1 is reduced.

Figure 10:
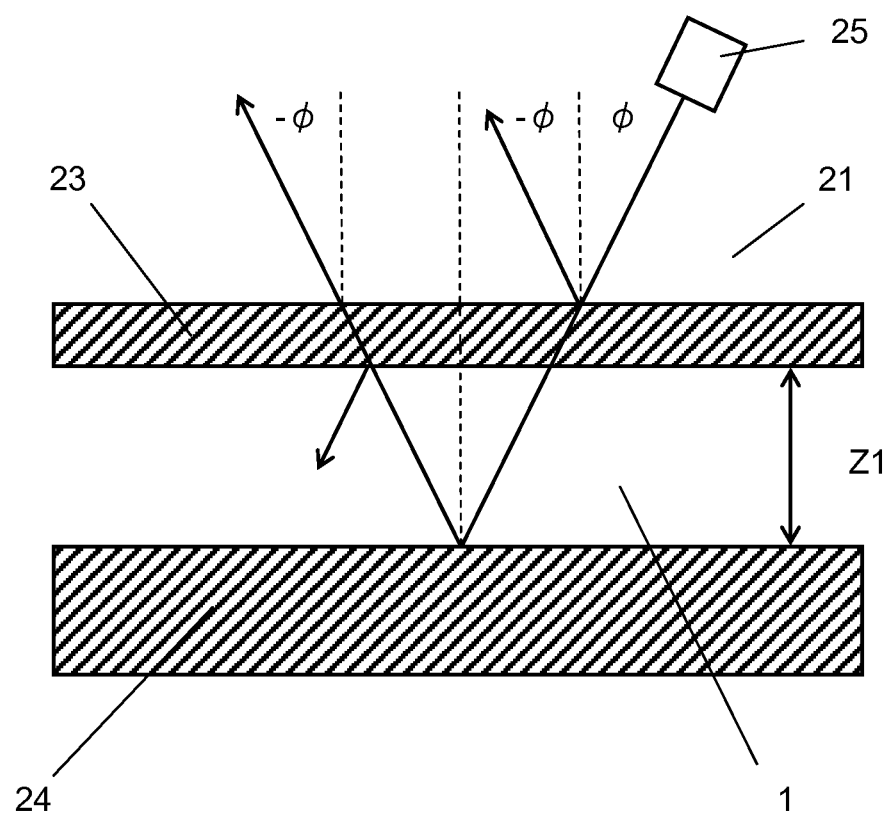
FIG. 10 is a schematic view of an electromagnetic wave propagating in a detection region of the flow channel device in accordance with the second exemplary embodiment.
Figure 11:
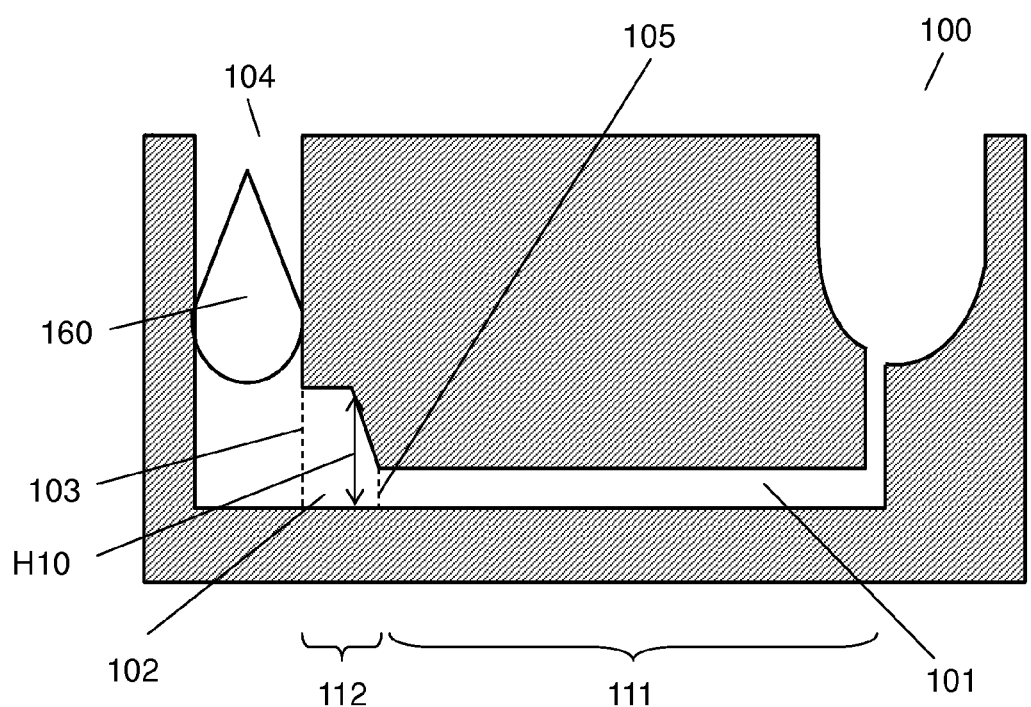
FIG. 11 is a schematic sectional view of a conventional flow channel device.

FIG. 10 is a schematic view of an electromagnetic wave propagating in detection region 21 of flow channel device 28 in accordance with the second exemplary embodiment. A part of the electromagnetic wave entering at angle φ from the part above first metal layer 23 is reflected by first metal layer 23, and propagates upward from first metal layer 23 in a direction of angle −φ. Herein, an angle between the vertical direction of first metal layer 23 and the direction in which an electromagnetic wave enters is referred to as φ. An angle symmetrical to angle φ with respect to the vertical direction of first metal layer 23 is referred to as −φ. Hereinafter, among electromagnetic waves entering from the part above first metal layer 23, an electromagnetic wave reflected by first metal layer 23 and propagating upward from first metal layer 23 in the direction of angle −φ is referred to as a first electromagnetic wave.

Most of the electromagnetic waves that have not been reflected by first metal layer 23 pass through first metal layer 23, propagate in flow channel 1, and reach second metal layer 24. When the thickness of second metal layer 24 is sufficiently large such as 100 nm or more, all of the electromagnetic waves reaching second metal layer 24 are reflected by second metal layer 24, and propagate in flow channel 1 toward first metal layer 23 again. Then, a part of electromagnetic waves reaching first metal layer 23 passes through first metal layer 23 and propagates upward from first metal layer 23 in the direction of angle −φ. Hereinafter, the electromagnetic wave which passes through first metal layer 23 from detection region 21, is reflected by second metal layer 24, and propagates to the part above first metal layer 23 in the direction of angle −φ is referred to a second electromagnetic wave.

Furthermore, most of electromagnetic waves reflected by second metal layer 24, reaching first metal layer 23, but not passing through first metal layer 23 are reflected by first metal layer 23, and then propagate in flow channel 1 toward the lower part again.

Herein, the first electromagnetic wave and the second electromagnetic wave interfere with each other above first metal layer 23. When the condition represented by mathematical formula Math. 1 is satisfied, the first electromagnetic wave and the second electromagnetic wave weaken each other. When the condition represented by mathematical formula Math 2 is satisfied, the first electromagnetic wave and the second electromagnetic wave strengthen each other. In the formulae, λ denotes wavelength of an electromagnetic wave, Z1 denotes a distance between first metal layer 23 and second metal layer 24, n denotes refractive index inside flow channel 1, and m is an integer.

$$(m+\tfrac{1}{2}) \times \lambda = 2 \times n \times z \times \cos\phi \quad \text{[Math 1]}$$

$$m \times \lambda = 2 \times n \times z \times \cos\phi \quad \text{[Math 2]}$$

Such interference conditions are controlled by distance Z1 between first metal layer 23 and second metal layer 24, and refractive index n of sample 60 inside flow channel 1, and the like.

A sensing section (not shown) for sensing electromagnetic waves such as light is disposed above first metal layer 23. Electromagnetic waves from electromagnetic wave source 25 are reflected or radiated by flow channel device 28. The reflected or radiated electromagnetic waves are received by the sensing section. Note here that the sensing section is not necessarily required. When the electromagnetic wave is visible light, a change of color or strength of the electromagnetic waves can be visually sensed with a user's own eyes. Thus, a simple and low-cost sensor device can be achieved. Note here that a flow channel device of this exemplary embodiment can be used for devices such as a sensor device and a mixing device, for handling fluid.

INDUSTRIAL APPLICABILITY

A flow channel device in this exemplary embodiment enables a sample containing a detection object to be efficiently introduced into a fine flow channel with a simple configuration. Therefore, the flow channel device can be used for highly sensitive and low-cost biosensors or the like.

The invention claimed is:

1. A detection method using a flow channel device, the method comprising the steps of:
preparing a solution including a detection object and a solid matter larger than the detection object,
introducing the solution into an introduction port inside the flow channel device;
allowing the solution to flow into an introduction channel inside the flow channel device;
allowing the detection object to flow into a flow channel inside the flow channel device and disabling the solid matter to flow into the flow channel; and
detecting the detection object inside the flow channel,
wherein the flow channel device includes:
a flow channel section including the flow channel in which the detection object flows and a wall surface surrounding the flow channel; and
an introduction channel section including the introduction channel having a first end connected to the flow channel and a second end connected to the introduction port, and a wall surface surrounding the introduction channel,
wherein in a shortest direction among directions perpendicular to a direction in which the detection object flows in the flow channel, when wall surfaces facing each other with the flow channel sandwiched therebetween, of the wall surface surrounding the flow channel, are defined as a first wall surface and a second wall surface, and a wall surface adjacent to the first wall surface and a wall surface adjacent to the second wall surface, of the wall surface surrounding the introduction channel, are defined as a third wall surface and a fourth wall surface,
at least a part of the third wall surface is a curved surface protruding toward the introduction channel,
a distance between the third wall surface and the fourth wall surface is larger than a size of the solid matter at the second end of the introduction channel, and
the distance between the third wall surface and the fourth wall surface is smaller than the size of the solid matter at the first end of the introduction channel such that the solid matter is stopped between the third wall surface and the fourth wall surface in the introduction channel at a different place in the direction in which the detection object flows depending upon a dimension of the solid matter.

2. The detection method of claim 1, wherein a diameter of the detection object is 2 µm or less.

3. The detection method of claim 1, wherein the detection object includes a first aggregate comprising fine particles modified with an antibody and antigen bound to the antibody, the solid matter includes a second aggregate comprising fine particles modified with the antibody and the antigen bound to the antibody, and the second aggregate is larger than the first aggregate.

* * * * *